US00PP13464P2

(12) United States Plant Patent
White

(10) Patent No.: US PP13,464 P2
(45) Date of Patent: Jan. 7, 2003

(54) PHYGELIUS PLANT NAMED 'BLAPHY'

(76) Inventor: Anthony Robin White, Kilmeston, Alresford, Hampshire SO24 0NL (GB)

( * ) Notice: Subject to any disclaimer, the term of this patent is extended or adjusted under 35 U.S.C. 154(b) by 0 days.

(21) Appl. No.: 09/957,706

(22) Filed: Sep. 19, 2001

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—Mark P. Bourgeois

(57) ABSTRACT

A new cultivar of Phygelius named 'Blaphy' that is characterized by an upright habit, reddish-purple pendulous flowers, burgundy stems and green leaves. In combination these traits set 'Blaphy' apart from all other existing varieties of Phygelius known to the inventor.

2 Drawing Sheets

BOTANICAL CLASSIFICATION

Phygelius.

VARIETY DENOMINATION

'Blaphy'.

BACKGROUND OF THE INVENTION

The present invention relates to a new and distinct cultivar of Phygelius, that is grown for its ornamental pendulous flowers and burgundy stems. The new cultivar is known botanically as *Phygelius×rectus* and will be referred to hereinafter by the cultivar name 'Blaphy'.

'Blaphy' is a hybrid and was bred by the inventor in a cultivated area of Hampshire, England. In 1996 the inventor crossed *Phygelius capensis* with *Phygelius aequalis* 'Sensation' (unpatented). The resulting hybrid was *Phygelius×rectus*. In 1997 the inventor crossed *Phygelius×rectus* with *Phygelius aequalis* 'Sensation'. A number of seedlings in various colors resulted from this second cross, seven of which exhibited rosy-purple coloring. From these seven the inventor selected *Phygelius×rectus* 'Blaphy' in 1998. The distinguishing characteristics of 'Blaphy' are flower color, stem size and color, and the arrangement of the flowers, which is predominately all around the stem, compared with a predominantly one-sided arrangement of the flowers which is typical of all species and cultivars of Phygelius known to the inventor. The top growth of 'Blaphy' tolerates temperatures of minus 5° Centigrade to minus 8° Centigrade, while the underground stolons tolerate lower temperatures. As a result 'Blaphy' can be used as a taller shrub in mild climates and as an herbaceous perennial in colder climates.

The closest comparison plants are the parents *Phygelius×rectus* and the commercial cultivar *Phygelius aequalis* 'Sensation'. 'Blaphy' is distinguishable from *Phygelius×rectus* by its flower color. The flowers of *Phygelius×rectus* are a mid tan color, close to RHS 48A. 'Blaphy' is distinguishable from *Phygelius aequalis* 'Sensation' by its flower size (diameter of flower apex of 'Sensation' does not exceed 1.0 cm), color (color of outside corolla of 'Sensation' is lighter purple, varies between RHS67A and RHS67B), stem size (stems of 'Sensation' are thinner, diameters in the range 0.2 cm to 0.3 cm, color is less dark, approximates to 187C) and sepal size (Sepals of 'Sensation' are longer and narrower, approximately 0.7 cm long and 0.15 cm wide).

'Blaphy' was first asexually propagated by the inventor in Hampshire, England in 1998 using softwood cuttings. Since that time, under careful observation, the distiguishing characteristics have been determined stable and uniform in successive generations.

SUMMARY OF THE INVENTION

The following represent the distinguishing characteristics of the new Phygelius cultivar 'Blaphy'. In combination these traits set 'Blaphy' apart from all other existing varieties of Phygelius known to the inventor. 'Blaphy' has not been tested under all possible conditions and phenotypic differences may be observed with variations in environmental, climatic, and cultural conditions, however, without any variance in genotype.

1. Phygelius 'Blaphy' is 90–120 cm. in height and equally as wide spreading by underground stolons.
2. Phygelius 'Blaphy' exhibits reddish-purple flowers in spring and summer.
3. Phygelius 'Blaphy' exhibits green leaves and burgundy stems.
4. Phygelius 'Blaphy' tolerates temperatures of minus 5° Centigrade to minus 8° Centigrade.
5. Phygelius 'Blaphy' exhibits an arrangement of flowers being predominantly all around the stem.

BRIEF DESCRIPTION OF THE DRAWINGS

The accompanying color photographs illustrate the distinguishing traits of the new Phygelius cultivar 'Blaphy'. The plants in the photographs were grown out-of-doors in Arroyo Grande, Calif. in two-gallon containers.

Sheet 1 is a color copy of an original photograph illustrating the entire plant in bloom from a side perspective.

Sheet 2 is a color copy of an original photograph showing a close-up view of the flowers. All photographs were taken using conventional techniques and although foliage colors may appear different from actual colors due to light reflectance, they are as accurate as possible by conventional photography and conventional copying techniques.

BOTANICAL DESCRIPTION OF THE PLANT

The following is a detailed description of the Phygelius cultivar named 'Blaphy'. Data was collected in Arroyo Grande, Calif. from the inventor and from 12 month old plants grown out-of-doors in two-gallon containers. Color determinations are in accordance with The Royal Horticultural Society Colour Chart except where general color terms of ordinary dictionary significance are used. The growing requirements are similar to the species. Under normal growing conditions there are no known disease problems known to the inventor.

Botanical classification: *Phygelius×rectus* 'Blaphy'.
Common name: Cape Fuschia.
Uses: Landscape shrub in mild climates and herbaceous perennial in colder climates.
Parent: 'Blaphy' is a hybrid resulting from the induced hybridization of the following plants:
- *Female parent.*—*Phygelius×rectus.*
- *Male parent.*—*Phygelius aequalis* 'Sensation'.

Type: Ornamental shrub.
Vigor: Vigorous.
Habit: Upright.
Height: 40 cm. in height.
Width: 40 cm. in width.
Hardiness: USDA Zone 8.
Propagation: Softwood cuttings.
Root system: Fibrous.
Soil: Plant in well-drained soils.
Sunlight: Plant in full sunlight.
Plant sexuality: Bisexual.
Time to initiate roots: 2 weeks are required for an initial cutting to produce roots.
Crop time: 4–8 months are required to produce a finished one-gallon from a rooted cutting.
Seasonal interest: Flowers in spring and summer.
Stem:
- *Branching habit.*—Pachycaul with shoots that are erect.
- *Internode length.*—4 cm. between nodes.
- *Stem diameter.*—0.50 cm. near base and 0.25 cm. near tip.
- *Stem length.*—24 cm. in length.
- *Shape.*—Quadrilateral with ridges at corners.
- *Surface.*—Glabrous.
- *Texture.*—Suffruticose at the base and soft toward tips of stems.
- *Stem color.*—187A.

Foliage:
- *Type.*—Evergreen.
- *Leaf arrangement.*—Opposite and spiral on stem.
- *Leaf division.*—Simple.
- *Leaf shape.*—Lanceolate.
- *Leaf base.*—Cuneate.
- *Leaf apex.*—Acute.
- *Leaf venation.*—Pinnate.
- *Vein color* (*adaxial and abaxial surfaces*).—187B.
- *Leaf attachment.*—Petiolate.
- *Petiole dimensions.*—2.5 cm. in length and 3 mm. in diameter.
- *Petiole color.*—187B.
- *Stipules.*—Present.
- *Color of stipules.*—138B.
- *Dimensions of stipules.*—1 mm. in width and 1 mm. in length.
- *Petiole shape.*—Quadrilateral with ridges at corners.
- *Leaf margin.*—Crenate.
- *Leaf texture.*—Soft and flexible.
- *Leaf length.*—7 cm. in length.
- *Leaf width.*—4 cm. in width.
- *Leaf color* (*adaxial surface*).—137A.
- *Leaf color* (*abaxial surface*).—138B.
- *Leaf surfaces* (*adaxial and abaxial*).—Glabrous and dull.
- *Foliar fragrance.*—Absent.

Flower:
- *Inflorescence.*—Spike.
- *Form.*—Solitary.
- *Persistent or self-cleaning.*—Self-cleaning.
- *Color of peduncle.*—187A.
- *Peduncle length.*—1.5 cm. in length.
- *Peduncle diameter.*—1 mm. in diameter.
- *Surface of peduncle.*—Glabrous.
- *Angle of peduncle to stem.*—45°.
- *Diameter of flower.*—0.5 cm at base; 1.0 cm. Below the apex.
- *Diameter of flower* (*apex*).—1.5 cm–1.8 cm.
- *Depth of flower* (*corolla tube*).—3.5 cm. in depth.
- *Length of flower* (*tube and lobes*).—4 cm. in length.
- *Shape.*—Tubular with five lobes.
- *Sexuality.*—Bisexual.
- *Aspect.*—Nutant.
- *Bud.*—Tubular and nutant.
- *Bud color.*—61A.
- *Petals.*—Five in number.
- *Fused or unfused.*—Petals are fused.
- *Petal margin.*—Minutely ciliate.
- *Color of corolla tube* (*inside surface*).—162D with veins of 187A.
- *Color of corolla tube* (*outside surface*).—61B.
- *Calyx dimensions.*—0.75 cm. in diameter and 0.75 cm. in height.
- *Calyx surface.*—Glabrous.
- *Calyx color.*—187A.
- *Sepals.*—Five in number.
- *Fused or unfused.*—Sepals are basally fused.
- *Sepal apex.*—Acute.
- *Sepal dimensions.*—3 mm. in diameter and 6 mm. in length.
- *Blooming period.*—Spring and summer.
- *Fragrance.*—Absent.

Reproduction organs:
- *Stamens.*—Four in number adnate to corolla tube and exserted.
- *Filament attachment to anther.*—Dorsifixed.
- *Color of stamen.*—187A.
- *Dimensions of stamen.*—1 cm. in length and 2 mm in diameter.
- *Anther surface.*—Furrowed and canaliculated on ventral surface.
- *Dimensions of anther.*—2 mm. in width and 3 mm. in length.
- *Pollen color.*—160A.
- *Anther color.*—160A.
- *Anther shape.*—Oblong.
- *Pistil.*—One.
- *Color of pistil.*—187B.

*Dimensions of pistil.*—4 cm. in length and less than 1 mm. in diameter.

*Ovary position.*—Superior.

*Ovary color.*—187A.

*Ovary dimensions.*—6 mm. in height and 3 mm. in width.

*Ovary shape.*—Piriform.

Seed: Seed has not been observed to date.

I claim:

1. A new and distinct variety of Phygelius plant named 'Blaphy' as described and illustrated.

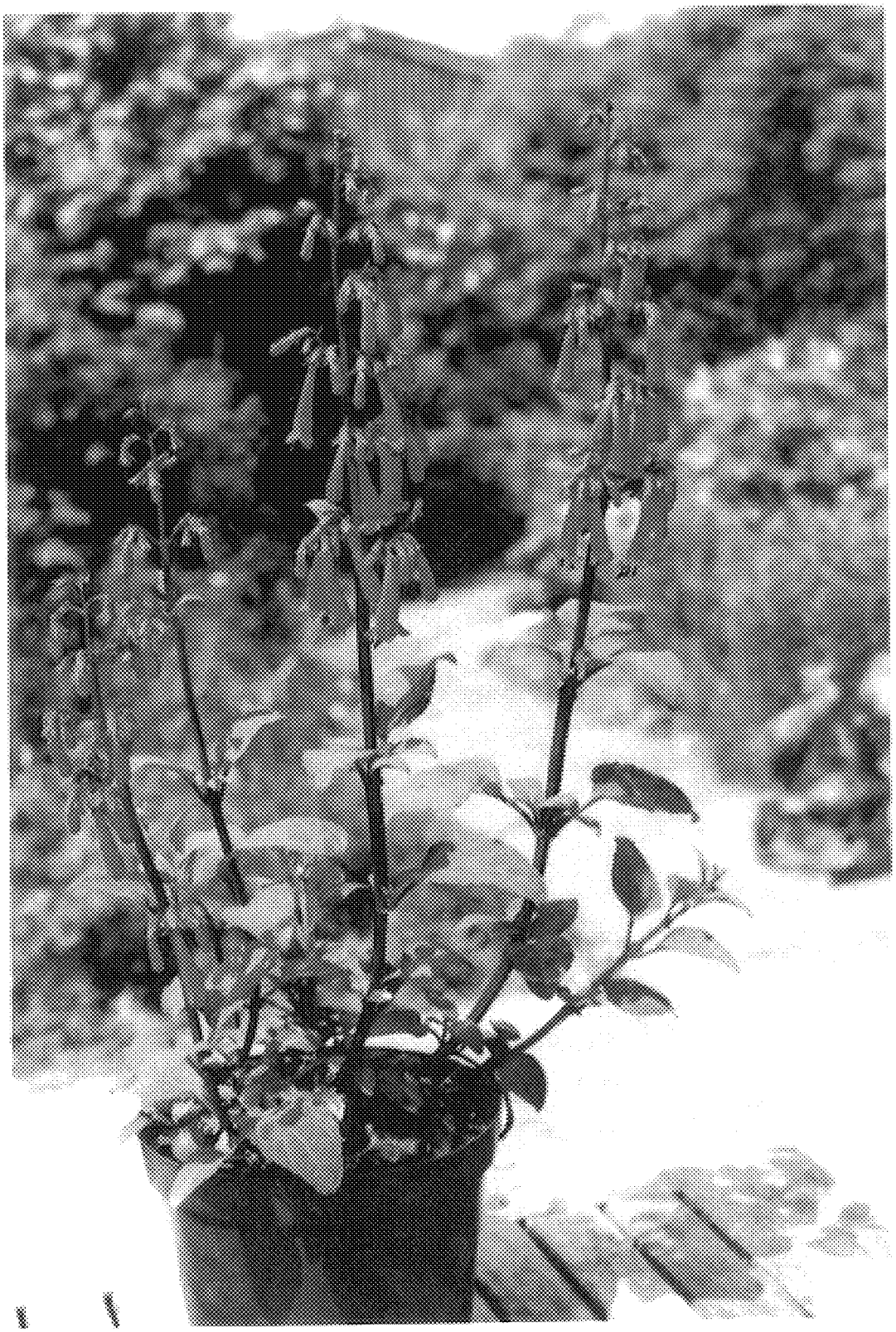

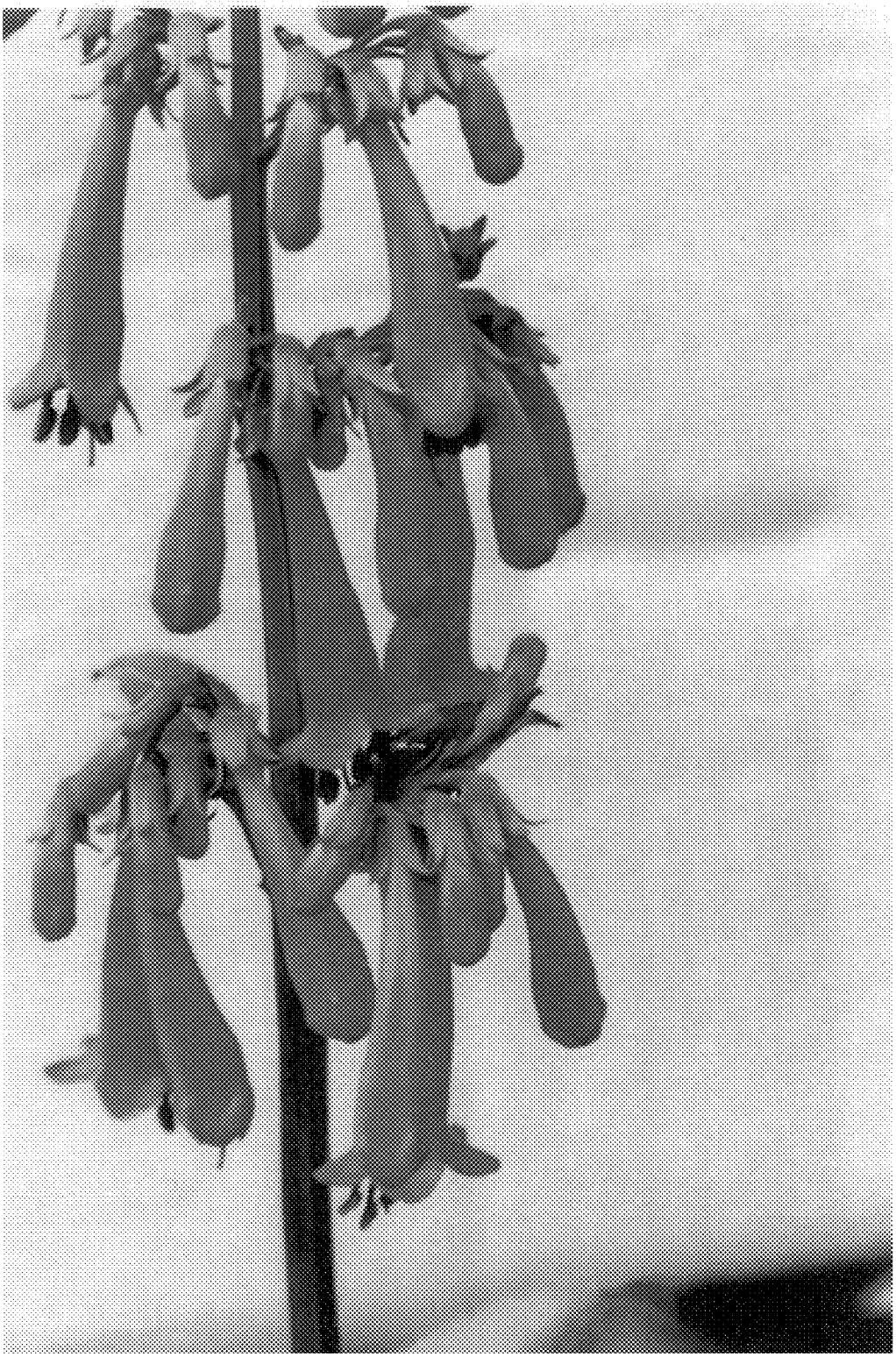

* * * * *